(12) United States Patent
Jahedshoar et al.

(10) Patent No.: US 6,602,494 B1
(45) Date of Patent: Aug. 5, 2003

(54) TRANSPARENT WATER-SILICON HAIR CONDITIONING AGENT

(75) Inventors: Mehrdad Jahedshoar, Calabasas, CA (US); Jennifer Imperial, Reseda, CA (US); Juergen Schmenger, Weiterstadt (DE); Karin Steinbrecht, Ober-Ramstadt (DE); Wilhelm Abels, Simi Valley, CA (US)

(73) Assignee: Wella AG, Darmstadt (DE)

( * ) Notice: Subject to any disclaimer, the term of this patent is extended or adjusted under 35 U.S.C. 154(b) by 212 days.

(21) Appl. No.: 09/868,550

(22) PCT Filed: Oct. 14, 2000

(86) PCT No.: PCT/EP00/10134

§ 371 (c)(1),
(2), (4) Date: Jan. 9, 2002

(87) PCT Pub. No.: WO01/28506

PCT Pub. Date: Apr. 26, 2001

(30) Foreign Application Priority Data

Oct. 21, 1999 (DE) .......................................... 199 50 711

(51) Int. Cl.[7] .............................. A61K 7/06; A61K 7/075
(52) U.S. Cl. ................ 424/70.1; 427/70.12; 427/70.27; 427/70.35; 427/401; 427/71.11; 427/70.19; 427/70.121; 427/70.122; 427/70.17; 427/70.21; 427/70.28; 514/937
(58) Field of Search .............................. 424/70.1, 70.12, 424/70.27, 70.31, 401, 70.11, 70.19, 70.121, 70.122, 70.17, 70.21, 70.28; 514/937

(56) References Cited

U.S. PATENT DOCUMENTS

| | | |
|---|---|---|
| 4,906,459 A | 3/1990 | Cobb |
| 5,332,569 A | 7/1994 | Wood et al. |
| 5,362,484 A | 11/1994 | Wood et al. |

FOREIGN PATENT DOCUMENTS

| | | |
|---|---|---|
| DE | 42 29 922 A1 | 3/1994 |
| DE | 195 18 449 A | 11/1995 |
| EP | 0 327 345 A | 8/1989 |
| EP | 0 397 245 A2 | 11/1990 |
| EP | 0 407 089 A | 1/1991 |
| EP | 0 490 582 A | 6/1992 |
| EP | 0 514 934 | * 11/1992 |
| EP | 0 514 934 A1 | 11/1992 |
| EP | 0 532 256 A1 | 3/1993 |
| EP | 0 847 748 A | 6/1998 |
| FR | 2 683 453 A | 5/1993 |
| WO | 93/19723 | 10/1993 |
| WO | 93/25179 | * 12/1993 |
| WO | 95/23581 | 9/1995 |

OTHER PUBLICATIONS

Schrader: "Grundlagen Und Rezepturen Der Kosmatika", 2. Auflage, 1989, pp. 728–737.
e. Flick: "Cosmetic and Toiletry Formulations", Second Edition, vol. 2, pp. 373–379.

* cited by examiner

*Primary Examiner*—Thurman K. Page
*Assistant Examiner*—Blessing Fubara
(74) *Attorney, Agent, or Firm*—Michael J. Striker

(57) ABSTRACT

An optically clear, transparent or translucent hair conditioner in the form of a water-in-silicone oil emulsion is described. Said hair conditioner contains a silicone surfactant, a hydrophobic, nonsurfactant silicone compound present in the hair conditioner in liquid form, a basic or cationic nitrogen atom-containing hair-conditioning compound, a nonionic, silicone-free surfactant, a polyhydric alcohol and an electrolyte. The hair conditioner can be used as a leave-in hair treatment or as a hair rinse.

16 Claims, No Drawings

TRANSPARENT WATER-SILICON HAIR CONDITIONING AGENT

This application is a 371 of PCT/8900/10134 filed Oct. 14, 2000.

The object of the invention is a hair conditioner which, in particular, can be used as a leave-in hair treatment or as a hair rinse, is in the form of an optically clear, transparent or at least translucent product and contains a silicone surfactant, a hydrophobic, nonsurfactant silicone compound present in the hair conditioner in liquid form, a basic or cationic nitrogen atom-containing hair conditioning compound and a nonionic, silicone-free surfactant.

As a rule, conventional hair-conditioning preparations such as rinse-off treatments or leave-on treatments are formulated on the basis of aqueous emulsions. Essential ingredients are cationic substances, for example cationic surfactants, hydrophobic substances, such as fatty alcohols and other oil components, emulsifiers and other specific agents and odorants. The most important ingredients are the cationic surfactants, fatty alcohols and emulsifiers. Schrader provides a review of the basic formulations of rinses and hair treatments in "Grundlagen und Rezepturen der Kosmetika" [Fundamentals and Formulations of Cosmetics], 2nd edition, 1989, pp. 728–737. The main function of hair conditioners is to improve the stylability, compatibility, luster and feel of the treated hair. The treated hair often feels somewhat heavier or more highly loaded, which is not always desirable. Moreover, the conventional oil-in-water [O/W] hair-care emulsions are normally milky white and opaque. Desirable are products which are in an optically more attractive form and clear, transparent or at least translucent. Various forms of clear hair-care compositions are known and described, for example, in E. Flick, "Cosmetic and Toiletry Formulations", second edition, volume 2, pp. 373 ff. These clear hair-care compositions are based on polymers with a thickening action such as, for example, cellulose derivatives (tradenames Natrosol®, Methocel®), high-molecular-weight chitosan derivatives (tradename Kytamer® PC), complex polysaccharides (tradenames karaya gum, tragacanth, Jaguar® brands, Keltrol® brands) and acrylic acid polymers. All these prior art clear hair-care compositions have the serious drawback that their efficacy is so low that it does not even come close to that of a conventional hair-care compositions based on a mixture of a fatty alcohol and a quaternary surfactant. Moreover, the distributability of these clear products is not as good as that of conventional O/W hair-care emulsions. For this reason, these clear hair-care compositions known from the prior art do not sell as well as do the standard products.

The goal was therefore to provide a composition which meets the typical requirements placed on hair conditioners in terms of hair conditioning and distributability and at the same time is in an optically attractive, particularly optically clear or at least translucent form. We have now found that this goal can be reached by means of a hair conditioner having the composition described hereinbelow. The object of the invention is an optically clear, transparent or translucent hair conditioner in the form of a water-in-silicone oil emulsion containing (A) at least one silicone surfactant selected from among the siloxane/polyoxyalkylene copolymers, (B) at least one hydrophobic nonsurfactant silicone compound present in the hair conditioner in liquid form, (C) at least one basic or cationic nitrogen atom-containing hair-conditioning compound, (D) at least one nonionic silicone-free surfactant, (E) 15 to 50 wt. % of water, (F) 15 to 50 wt. % of at least one polyhydric alcohol and (G) at least one electrolyte.

The entire silicone oil phase preferably represents less than 40 wt. % and particularly less than 20 wt. %, and the aqueous phase preferably more than 60 wt. % and particularly more than 80 wt. % of the overall composition. The hair conditioner meets very satisfactorily the requirements placed on hair conditioners in terms of conditioning action. The hair conditioner distributes itself readily on the hair. After the treatment, the hair is appreciably smoother and softer both in the wet and in the dry condition. The compatibility and stylability of the hair is better, and the hair is disentangled and lustrous. Moreover, the composition according to the invention makes it possible to produce the hair conditioner in an optically attractive, clear formulation which in turn permits advantageous packing in a transparent container made, for example, of glass or transparent plastic, for example polyethylene, polypropylene or polyethylene terephthalate.

The silicone surfactant (A) is present in the hair conditioner of the invention preferably in an amount from 0.01 to 10 wt. %, particularly from 0.1 to 5 wt. % and more preferably from 0.4 to 2 wt. %. Suitable silicones are the siloxane/polyoxyalkylene copolymers. These are siloxanes with polyalkylene oxide groups, particularly silicones modified with polypropylene oxide, polyethylene oxide or a mixture thereof. The alkylene oxide groups can be in a lateral or terminal position or the compounds can be linear polydimethylsiloxane/polyalkylene oxide block copolymers. The alkylene oxide-modified siloxanes have the INCI [International Nomenclature of Cosmetic Ingredients] designation "dimethicone copolyol". Preferred silicone surfactants are those of general formula (I)

$$A-B_x-D_y-A \qquad (I)$$

wherein

A stands for the monovalent group $R_2R^1SiO_{1/2}$

B denotes the divalent group $R_2SiO$,

D denotes the divalent group $RR^1SiO$,

R independent of each other denote H, $C_1$–$C_6$-alkyl or aryl, preferably H or $C_1$–$C_4$-alkyl and most preferably methyl, $R^1$ stands for an oxyalkylene-containing group, hydrogen or methyl, x denotes a numeral from 10 to 1000, preferably from 10 to 500 and particularly from 20 to 200, and y denotes a numeral from 0 to 100 and preferably from 1 to 50, providing that the compound contains at least one oxyalkylene-containing $R^1$ group.

The $R^1$ group preferably denotes a group of general formula (II)

$$-R^2(OC_nH_{2n})_mR^3 \qquad (II)$$

wherein $R^2$ is a divalent group linking the oxyalkylene unit to the siloxane chain, preferably $C_pH_{2p}$ wherein p equals 2–8, preferably 2–6 and particularly 3–6;

$R^3$ is a monovalent end group for the oxyalkylene unit, for example H, OH, $C_1$–$C_6$-alkyl, aryl, $C_1$–$C_6$-alkoxy, $C_1$–$C_6$-acyloxy, but preferably OH, n is a numeral from 2 to 4, and preferably 2 or 3, and m is a numeral denoting at least unity, the sum of m for all oxyalkylene groups being about 10 or higher.

Suitable silicone surfactants are commercially available, for example DC 3225 C, DC Q2-5220, DC 193, DC 190 or DC Q4-3667 from Dow Corning, Silwet® L-7200 from OSI Specialties, Abil® B8830, Abil® B8851, Abil® B8863 or Abil® EM97 from Goldschmidt, SF-1 188 from General Electric or KF 353A from Shin Etsu.

The hydrophobic nonsurfactant-silicone compound (B) is preferably present in an amount from 5 to 30 wt. %, particularly from 7.5 to 25 wt. % and more preferably from 10 to 20 wt. %. Suitable in principle are all silicone compounds with hair conditioning properties and which are insoluble in the aqueous phase. Said silicone compounds may be highly volatile and of low molecular weight or low-volatile and of high molecular weight. In a preferred embodiment, the hair conditioner contains at least one low-molecular-weight, highly volatile and at least one high-molecular-weight, nonvolatile or low-volatile silicone. Non-volatile silicones in the sense of this application are silicones with no or only low vapor pressure at normal ambient conditions (1 atmosphere, 25° C.). These silicones remain on the hair after they have been applied. Volatile silicones, on the other hand, vaporize after they have been applied to the hair, which under normal ambient condition typically occurs within a period of about 2 hours. The high-molecular-weight silicone, however, can also be a silicone polymer (silicone resin, silicone gum) dissolved in a low-molecular-weight liquid silicone. The viscosity of low-molecular-weight silicone oils is preferably from 100 to 1000 mPa s, and that of high-molecular-weight silicone oils from more than 1000 to 2,000,000 mPa s at 25° C., measured with a Haake, model VT 501, rotational viscometer at a shear rate of 12.9 per second. Suitable hydrophobic silicones are, in general, cyclic polydimethylsiloxanes (INCI designation: cyclomethicones), for example octamethylcyclotetrasiloxane and decamethylcyclopentasiloxane, linear polydimethylsiloxanes (INCI designation: dimethicones), polydiethylsiloxanes, phenyl-substituted siloxanes (INCI designation: phenyltrimethicones), polymethylphenylsiloxanes, hydroxy-substituted siloxanes (INCI designation: dimethiconols) or mixtures thereof.

The nitrogen-containing hair-conditioning compound (C) is preferably present in an amount from 0.01 to 10 wt. %, particularly from 0.1 to 5 wt. % and more preferably from 0.2 to 3 wt. %. The hair-conditioning compound is a substance which because of the primary, secondary, tertiary or quaternary amino groups exhibits substantivity to human hair. Suitable hair-conditioning compounds are those selected from among cationic surfactants, betaine surfactants, amphoteric surfactants, cationic polymers, cationically derivatized proteins or protein hydrolyzates, betaine and nitrogeh-containing silicone compounds. Particularly preferred are the hair conditioners of the invention which contain at least one cationic silicone-free surfactant and at least one nitrogen-containing silicone compound.

Suitable cationic surfactants are those containing a quaternary ammonium group. Such surfactants can be the cationic or amphoteric betaine surfactants. Cationic surfactants are particularly preferred as the cationic substance (A). Suitable cationic surfactants contain amino groups or quaternized hydrophilic ammonium groups which in solution bear a positive charge and are represented by general formula (III)

$$N^{(+)}R^1R^2R^3R^4 \ X^{(-)} \quad (III)$$

wherein
R$^1$ to R$^4$ independently of each other denote aliphatic groups, aromatic groups, alkoxy groups, polyoxyalkylene groups, alkylamido groups, hydroxyalkyl groups, aryl groups or alkaryl groups, each with 1 to 22 carbon atoms, and X$^{(-)}$ denotes a cosmetically compatible anion, for example a halogen, acetate, phosphate, nitrate or alkylsulfate, but preferably chloride.

For the compound to exhibit surfactant properties, at least one of the R$^1$ to R$^4$ groups must have at least 8 carbon atoms. In addition to the carbon atoms and hydrogen atoms, the aliphatic groups can also contain crosslinks or other groups, for example other amino groups.

Examples of suitable cationic surfactants are the chloride or bromide salts of alkyldimethyl-benzylammonium or alkyltrimethylammonium, for example cetyltrimethylammonium chloride or bromide, tetradecyltrimethylammonium chloride or bromide, alkyldimethylhydroxyethylammonium chlorides or bromides, dialkyldimethylammonium chlorides or bromides, the alkylpyridinium salts, for example laurylpyridinium or cetylpyridinium chloride, alkylamidoethyltrimethylammonium ether sulfate, and compounds of a cationic character, such as the amine oxides, for example alkylmethylamine oxides or alkylaminoethyldimethylamine oxides. Particularly preferred are cetyltrimethylammonium chloride, sold, for example, in the form of a 26% aqueous solution under the tradename Dehyquart® A by Cognis and under the tradename Genamin® CTAC by Clariant, and in the form of a 50% solution in isopropanol under the tradename Arquad® 16–50 by Akzo Nobel.

Suitable amphoteric surfactants are the derivatives of aliphatic quaternary ammonium, phosphonium and sulfonium compounds of formula (IV)

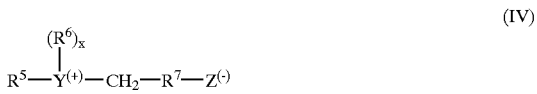

(IV)

wherein
R$^5$ is a linear or branched alkyl, alkenyl or hydroxyalkyl group with 8 to 18 carbon atoms, from 0 to about 10 ethylene oxide units and from 0 to 1 glycerol units, Y denotes an N-, P- or S-containing group, R$^6$ denotes an alkyl or monohydroxyalkyl group with 1 to 3 carbon atoms, x equals 1 when Y is a sulfur atom and it equals 2 when Y is a nitrogen or phosphorus atom, R$^7$ denotes an alkylene or hydroxyalkylene group with 1 to 4 carbon atoms, and Z$^{(-)}$ denotes a carboxylate, sulfate, phosphonate or phosphate group.

Other amphoteric surfactants such as the alkylbetaines are also suitable for the hair conditioner of the invention. Examples of betaines are C$_8$–C$_{18}$-alkylbetaines, such as cocodimethylcarboxymethylbetaine, lauryldimethylcarboxymethylbetaine, lauryldimethylalphacarboxyethylbetaine, cetyidimethylcarboxymethylbetaine, oleyldimethylgammacarboxypropylbetaine and laurylbis-(2-hydroxypropyl)-alphacarboxyethylbetaine; C$_8$–C$_{18}$-sulfobetaines, such as cocodimethylsulfopropylbetaine, stearyidimethylsulfopropylbetaine, lauryidimethylsulfoethylbetaine, laurylbis-(2-hydroxyethyl)-sulfopropylbetaine; the carboxyl derivatives of imidazole, the C$_8$–C$_{18}$-alkyldimethylammonium acetates, the C$_8$–C$_{18}$-alkyldimethylcarbonylmethylammonium salts and the $C_1$–$C_{18}$-fatty acid alkylamidobetaines, for example the coco fatty acid amidopropylbetaine which, for example, in the form of a 30% aqueous solution is sold by Goldschmidt AG under the tradename Tego® Betaine L7, and the N-coco fatty acid amidoethyl-N-[2-carboxymethoxy] ethyllglycerol (CTFA[1] name: cocoamphocarboxyglycinate) which, for example, in the form of a 50% aqueous solution is sold by Miranol Chemical Co., Inc. under the tradename Miranol® C2M.

[1] CTFA=Cosmetic, Toiletry and Fragrance Association—Translator

The suitable cationic polymers are preferably hair-fixing or hair-conditioning polymers. Suitable cationic polymers preferably contain quaternary amino groups. The cationic polymers can be homopolymers or copolymers in which the quaternary nitrogen groups are located either in the polymer chain or preferably as substituents on one or several of the monomer units. The ammonium groups-containing monomers can be copolymerized with noncationic monomers. Suitable cationic monomers are unsaturated compounds capable of undergoing free radical-initiated polymerization and bearing at least one cationic group, particularly ammonium-substituted vinyl monomers, for example trialkylmethacryloxyalkylammonium, trialkylacryloxyalkylammonium, dialkyldiallylammonium and quaternary vinylammonium monomers with cyclic, cationic, nitrogen-containing groups, such as pyridinium and imidazolium, or quaternary pyrrolidones, for example alkylvinylimidazolium, alkylvinylpyridinium, or alkylvinylpyrrolidone salts. The alkyl groups of these monomers are preferably lower alkyl groups, for example $C_1$–$C_7$-alkyl groups and particularly $C_1$-$C_3$-alkyl groups.

[1] CTFA=Cosmetic, Toiletry and Fragrance Association—Translator

The ammonium groups-containing monomers can be copolymerized with noncationic monomers. Suitable comonomers are, for example, acrylamide, methacrylamide, alkyl- and dialkylacrylamide, alkyl- and diacrylmethacrylamide, alkyl acrylate, alkyl methacrylate, vinylcaprolactone, vinylcaprolactam, vinylpyrrolidone, vinyl esters, for example vinyl acetate, vinyl alcohol, propylene glycol or ethylene glycol, the alkyl groups of these monomers preferably being $C_1$–$C_7$-alkyl groups and particularly $C_1$–$C_3$-alkyl groups.

Suitable polymers with quaternary amino groups are, for example, the polymers described in the CTFA Cosmetic Ingredients Dictionary under the polyquaternium names, such as methylvinylimidazolium chloride/vinylpyrrolidone copolymer (polyquaternium 16) or the quaternized vinylpyrrolidone/dimethyl-aminoethyl methacrylate copolymer (polyquaternium 11), and the quaternary silicone polymers or oligomers, such as, for example, the silicone polymers with quaternary end groups (quaternium 80).

Suitable cationic polymers that can be contained in the hair conditioners of the invention include, for example, vinylpyrrolidone/dimethylaminoethyl methacrylate methosulfate copolymer sold by ISP under the tradenames Gafquat® 755 N and Gafquat® 734, of which Gafquate 734 is particularly preferred. Other cationic polymers are, for example, the copolymer of polyvinyl pyrrolidone [sic—vinylpyrrolidone seems to be meant—Translator] and imidazolimine methochloride, sold by BASF, Germany, under the tradename LUVIQUAT® HM 550, the terpolymer of dimethyldiallylammonium chloride, sodium acrylate and acrylamide, sold by Calgon/USA under the tradename Merquat® Plus 3300, the terpolymer of vinylpyrrolidone, dimethylaminoethyl methacrylate and vinylcaprolactam sold by ISP/USA under the tradename Gaffix® VC 713 and the vinylpyrrolidone/methacrylamidopropyltrimethylammonium chloride copolymer sold by ISP under the tradename Gafquat® HS 100.

Suitable cationic polymers derived from natural polymers are the cationic derivatives of polysaccharides, for example the cationic derivatives of cellulose, starch or guar. Also suitable are chitosan and chitosan derivatives. Cationic polysaccharides have the general formula (V)

$$G\text{---}O\text{---}B\text{---}N^+R^aR^bR^c\ X^- \qquad (V)$$

wherein

G is an anhydroglucose radical, for example starch anhydroglucose or cellulose anhydro-glucose, B is a divalent linking group, for example alkylene, oxyalkylene, polyoxyalkylene or hydroxyalkylene, $R^a,R^b,R^c$ are independently of each other alkyl, aryl, alkylaryl, arylakyl, alkoxyalkyl or alkoxyaryl, each with up to 18 carbon atoms, the total number of carbon atoms in $R^a$, $R^b$ and $R^c$ preferably being at the most 20;

$x^-$ is a common counteranion, has the same meaning as in formula (III) and is preferably chloride.

A cationic cellulose is sold by Amerchol under the name Polymer JR and has the INCI designation polyquaternium 10. Another cationic cellulose has the INCI designation polyquaternium 24 and is sold by Amerchol under the tradename Polymer LM-200. A suitable cationic guar derivative is sold under the tradename Jaguar® R and has the INCI designation guar hydroxypropyltrimonium chloride. Particularly preferred cationic substances are chitosan, chitosan salts and chitosan derivatives. The chitosans used according to the invention are completely or partially deacetylated chitins. The preferred starting material for preparing chitosan is the chitin contained in the shell residues of crustaceans and which is available in large amounts as an inexpensive and natural raw material. The molecular weight of chitosan can be distributed over a broad range, for example from 20,000 to about 5 million g/mol. Suitable is, for example, a low-molecular-weight chitosan with a molecular weight of 30,000 to 70,000 g/mol. Preferably, however, the molecular weight is higher than 100,000 g/mol and particularly ranges from 200,000 to 700,000 g/mol. The degree of deacetylation is preferably 10 to 99% and particularly 60 to 99%.

A suitable chitosan is sold, for example, by Kyowa Oil & Fat, Japan, under the tradename Flonac®. It has a molecular weight of 300,000 to 700,000 g/mol and is 70 to 80% deacetylated. A preferred chitosan salt is chitosoniumpyrrolidone carboxylate sold, for example, by Amerchol, USA, under the tradename Kytamer® PC. The chitosan contained in this material has a molecular weight of about 200,000 to 300,000 g/mol and is 70 to 85% deacetylated. Suitable chitosan derivatives are the quaternized, alkylated or hydroxyalkylated derivatives, for example hydroxyethylchitosan or hydroxybutylchitosan.

The chitosans or chitosan derivatives are preferably in neutralized or partly neutralized form. The degree of neutralization of chitosan or a chitosan derivative is preferably at least 50% and particularly between 70 and 100%, based on the number of free basic groups. In principle, all cosmetically compatible inorganic or organic acids can be used as the neutralization agent, for example formic, tartaric, malic, lactic, citric, pyrrolidonecarboxylic or hydrochloric acid and the like. Among these, pyrrolidonecarboxylic acid is particularly preferred.

Other suitable cationic hair-care compounds are the cationically modified protein derivatives or cationically modified protein hydrolyzates known, for example, under the INCI designations lauryldimonium hydroxypropyl hydrolyzed wheat protein, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed silk, lauryidimonium hydroxypropyl hydrolyzed soy protein or hydroxypropyltrimonium hydrolyzed wheat, hydroxypropyltrimonium hydrolyzed casein, hydroxypropyltrimonium hydrolyzed collagen, hydroxypropyltrimonium hydrolyzed keratin, hydroxypropyltrimonium hydrolyzed rice bran protein, hydroxypropyltrimonium hydrolyzed silk, hydroxypropyltrimonium hydrolyzed soy protein and hydroxypropyltrimonium hydrolyzed vegetable protein.

Suitable cationically derivatized protein hydrolyzates are mixtures of substances obtainable, for example, by reaction of a protein hydrolyzed with an alkali, acid or enzyme and glycidyltrialkyl-ammonium salts or 3-halo-2-hydroxypropyltrialkylammonium salts. The proteins used as starting materials for the protein hydrolyzates can be of vegetable or animal origin. Common starting materials are, for example, keratin, collagen, elastin, soy protein, rice protein, milk protein, wheat protein, silk protein or almond protein. Hydrolysis affords mixtures of substances with molecular weights in the range from about 100 to about 50,000. The average molecular weights are usually in the range from about 500 to about 1000. Advantageously, the cationically derivatized protein hydrolyzates contain one or two long $C_8$–$C_{22}$-alkyl chains and, correspondingly, two or one short $C_1$–$C_4$-alkyl chain. Compounds containing one long alkyl chain are preferred.

Suitable cationically active silicone compounds are the cationic silicones, betaine silicones or amino-substituted silicones. They contain either at least one amino group or at least one ammonium group. Suitable silicone polymers with amino groups are known under the INCI designations amodimethicone and trimethylsilylamodimethicone. These are polydimethylsiloxanes with aminoalkyl groups. The aminoalkyl groups can be lateral or terminal. Suitable aminosilicones are those of general formula (VI)

$$R^8R^9R^{10}Si{-}(OSiR^{11}R^{12})x{-}(OSiR^{13}Q)\ y{-}OSiR^{14}R^{15}R^{16} \quad (VI)$$

wherein $R^8$, $R^9$, $R^{14}$ and $R^{16}$ independently of each other are equal or different and denote $C_1$–$C_{10}$-alkyl, phenyl, hydroxyl, hydrogen, $C_1$–$C_{10}$-alkoxy or acetoxy, preferably $C_1$–$C_4$-alkyl and particularly methyl, $R^{10}$ and $R^{16}$ independently of each other are equal or different and denote —$(CH_2)_a$—$NH_2$ where a equals 1 to 6, $C_1$–$C_{10}$-alkyl, phenyl, hydroxyl, hydrogen, $C_1$–$C_{10}$-alkoxy or acetoxy, preferably $C_1$–$C_4$-alkyl and particularly methyl, $R^{11}$, $R^{12}$, $R^{13}$ independently of each other are equal or different and denote hydrogen, a $C_1$–$C_{20}$-hydrocarbon group which can contain O- and N-atoms, but preferably $C_1$–$C_{10}$-alkyl or phenyl, particularly $C_1$–$C_4$-alkyl and especially methyl, Q denotes —A—$NR^{17}R^{18}$, or —A—$N+R^{17}R^{18}R^{19}$ where A stands for a divalent $C_1$–$C_{20}$-alkylene linking group which can also contain O- and N-atoms and OH groups, and $R^{17}$, $R^{18}$ and $R^{19}$ independently of each other are equal or different and denote hydrogen, a $C_1$–$C_{22}$ hydrocarbon group and preferably $C_1$–$C_4$ alkyl or phenyl. The preferred Q radicals are —$(CH_2)_3$-$NH_2$, —$(CH_2)_3NHCH_2CH_2NH_2$, —$CH_2CH(CH_3)$ $CH_2NHCH_2CH_2NH_2$, —$(CH_2)_3OCH_2CHOHCH_2NH_2$, —$(CH_2)_3N(CH_2CH_2OH)_2$, —$(CH_2)_3$-$NH_3^+$ and —$(CH_2)_3OCH_2CHOHCH_2N^+$ $(CH_3)_2R^{20}$, where $R^{20}$ is a $C_1$–$C_{22}$-alkyl radical that can also contain OH groups, x is a numeral from 1 to 10,000, preferably from 1 to 1000, and y denotes a numeral between 1 and 500 and preferably between 1 and 50.

The molecular weight of the aminosilicones is preferably between 500 and 100,000. The amine content (meq/g) is preferably in the range from 0.05 to 2.3 and particularly from 0.1 to 0.5.

Suitable silicone polymers with two terminal quaternary ammonium groups are known under the INCI designation quaternium 80. These are dimethylsiloxanes with two terminal aminoalkyl groups. Suitable quaternary aminosilicones are those of general formula (VII)

$$R^{21}R^{22}R^{23}N^+{-}A{-}SiR^8R^9{-}(OSiR^{11}R^{12})_n{-}OSiR^8R^9{-}A{-}N^+\\ R^{21}R^{22}R^{23}\ 2X^- \qquad VII$$

wherein

A has the same meaning as indicated hereinabove for formula (VI) and is preferably —$(CH_2)_3OCH_2CHOHCH_2$ in combination with the $N^+(CH_3)_2R^{20}$ group, where $R^{20}$ is a $C_1$–$C_{22}$-alkyl radical which can also contain OH groups, $R^8$,$R^9$,$R^{11}$,$R^{12}$ have the same meaning as indicated hereinabove for formula (VI) and preferably denote methyl, $R^{21}$,$R^{22}$, $R^{23}$ independently of each other denote $C_1$–$C_{22}$-alkyl radicals which can contain hydroxyl groups and wherein preferably at least one of the radicals contains at least 10 carbon atoms and the remaining radicals contain from 1 to 4 carbon atoms, and n is a numeral from 0 to 200 and preferably from 10 to 100.

Such diquaternary polydimethylsiloxanes are sold by Goldschmidt under the tradenames Abil® Quat 3270, 3272 and 3274.

The nonionic, silicone-free surfactant (D) is preferably present in the hair conditioner in an amount from 0.01 to 5 wt. %, particularly from 0.1 to 2 wt.0h and most preferably from 0.2 to 1 wt. %. Suitable nonionic surfactants are, for example, those described in the "International Cosmetic Ingredient Dictionary and Handbook", 7th edition, vol. 2, in the chapter on "Surfactants—Emulsifying Agents". Suitable nonionic surfactants are preferably selected from among ethoxylated fatty acids with 10 to 26 carbon atoms, ethoxylated monohydric or polyhydric alcohols with 1 to 6 carbon atoms, ethoxylated fatty alcohols with 10 to 26 carbon atoms, ethoxylated hydrogenated or nonhydrogenated castor oil, alkylpolyglucosides, glyceride alkoxylates, fatty acid glyceride polyalkylene glycol ethers or fatty acid partial glyceride polyalkylene glycol ethers, each with less than 30 alkylene glycol units. Examples of these are polyethylene glycol(7) glyceryl cocoate, polyglycolamides, fatty acid sugar esters, ethoxylated fatty acid sugar esters and partial glycerides. The degree of ethoxylation of the ethoxylated surfactants is usually from 1 to 400, particularly from 2 to 200 and most preferably from 3 to 25. Preferred nonionic surfactants are, in particular, the fatty alcohol ethoxylates. Suitable are, for example, alcohols with 10 to 18 and preferably with 10 to 16 carbon atoms, and a preferred degree of ethoxylation of 2 to 200 and particularly 3 to 25. The nonionic surfactants preferably have a relatively high $HLB^2$ value of at least 9.

[2] HLB=hydrophilic-lipophilic balance—Translator

The water content preferably ranges from 15 to 50 wt. %, particularly from 15 to 40 wt. % and most preferably from 15 to 39 wt. %. The aqueous phase of the hair conditioner of the invention contains as a cosolvent at least one cosmetically compatible polyhydric alcohol. Suitable polyhydric alcohols are, in particular, those with 2 to 4 carbon atoms, for example, ethylene glycol or propylene glycol, but also sorbitol, with glycerol being particularly preferred. The polyhydric alcohols are preferably used in an amount from 5 to 50 wt. %, particularly from 10 to 40 wt. % and most preferably from 15 to 39 wt. %. Moreover, the hair conditioner can also contain lower monohydric alcohols with 1 to 4 carbon atoms commonly used for cosmetic purposes, for example ethanol and isopropanol.

The hair conditioner of the invention is preferably in the form of a microemulsion. To achieve a particularly clear product, the refractive indices of the oil phase and the aqueous phase are adjusted to be essentially equal. Particular characteristics of the hair conditioner of the invention are its outstanding clarity and transparency. Hence, the hair conditioner is advantageously packaged in optically attractive containers made of transparent or translucent material. Suitable packaging materials are, in particular, glass and transparent or translucent plastics, for example polyethylene terephthalate.

For increased emulsion stability, the hair conditioner of the invention contains water-soluble electrolytes, for example sodium chloride or sodium sulfate. The electrolytes are preferably used in an amount from 0.01 to 5, particularly from 0.1 to 4 and most preferably from 0.5 to 1.5 wt. %. The pH of the hair conditioner of the invention is preferably in the acid range, for example between 2.0 and 6.0. Particularly preferred is the pH range of 3.5–4.5. The pH can be adjusted with suitable organic or inorganic acids, for example with formic, tartaric, malic, maleic, fumaric, pyrrolidone-carboxylic, citric, lactic, sulfuric, acetic, hydrochloric, phosphoric and glyoxylic acid, among others.

The hair conditioner of the invention can also contain the usual additive components for hair-care compositions, for example fixing or nonfixing nonionic, anionic, cationic, zwitterionic or amphoteric polymers as well as combinations thereof, preferably in an amount of 0.01 to 10 wt. %, the polymer possibly being synthetic or of natural origin; perfume oils preferably in an amount from 0.01 to 5 wt. %; other wetting agents or emulsifiers from the classes of anionic, cationic, amphoteric or nonionic surface-active substances, preferably in an amount from 0.01 to 10 wt. %; moisturizing agents, preservatives, bactericidal and fungicidal agents, for example 2,4,4-trichloro-2-hydroxydiphenyl ether, parabens or methylchloroisothiazolinone in an amount from 0.01 to 1.0 wt. %; buffering agents, for example sodium citrate or sodium phosphate, in an amount from 0.1 to 1.0 wt. %; colorants, for example fluorescein sodium salt, in an amount from about 0.1 to 1.0 wt. %; cosmetic care agents, for example plant and herb extracts, protein and silk hydrolyzates, lanolin derivatives, in an amount from 0.1 to 5 wt. %, and furthermore sunscreen agents, antioxidants, free-radical scavengers, anti-dandruff agents, fatty alcohols, luster-imparting agents, vitamins and fat-restoring agents, in an amount from 0.01 to 10 wt. %.

The hair conditioner can be in the form of a lotion or a thickened lotion of varying viscosity or in the form of a highly viscous or fluid gel or a liquid gel.

If the hair conditioner is in the low-viscosity form, it can also be sprayed onto the hair to achieve especially good distribution. The hair conditioner according to the invention is then used in conjunction with a suitable mechanically actuated spraying device. By mechanical spraying device is meant a device permitting the spraying of a liquid without the use of a propellant. A suitable mechanical spraying device is, for example, a spray pump or a spray valve-bearing elastic container into which the hair conditioner of the invention is introduced under pressure causing the container to expand. When the valve is opened, the hair conditioner is steadily released as a result of the contraction of the elastic container.

The hair conditioner can be used as a rinse-off or as a leave-on product. A typical application as rinse-off product involves distributing an amount of hair conditioner, sufficient to achieve a desired conditioning effect after washing the hair, into or onto wet or moist, towel-dried hair. The amount to be used depends on the fullness of the hair and typically ranges from 1 to 25 g and preferably from 3 to 10 g. After a sufficient exposure time of, for example, 1 to 15 minutes, the hair is rinsed. If only a gentle conditioning effect is desired, the rinsing may also be done immediately. The hair is then optionally combed or formed into a hair style and dried. For use as a leave-on product, 0.5 to 3 g of the product is preferably worked into the dry hair. As a result, the cuticulae are smoothed out, the undesirable entanglements are removed, and luster, stylability, control and structure are conferred to the hair.

The following examples illustrate the object of the invention in greater detail.

EXAMPLE 1

CLEAR HAIR CONDITIONER 16.0 g of cyclomethicone (Dow Corning 345)

6.0 g of Dow Corning 3225C (dimethicone copolyol, 10% in cyclomethicone)

0.75 g of phenyltrimethicone (Dow Corning Fluid 556)

1.0 g of dimethicone (Dow Corning 200, 500 cps)

0.5 g of dimethicone (Dow Corning 200, 60,000 cps)

0.5 g of Dow Corning 1401 (dimethiconol, 13% in cyclomethicone)

0.5 g of trimethylsilylamodimethicone (Dow Corning Q2-8220)

1.0 g of cetyltrimethylammonium chloride 0.5 g of Cremophor RH410 (PEG-40 hydrogenated castor oil)

0.8 g of sodium chloride 0.1 g of citric acid q.s. of perfume, preservative 34.0 g of glycerol to 100 g water

EXAMPLE 2

CLEAR HAIR CONDITIONER 7.0 g of cyclomethicone (Dow Corning 345)

10.0 g of Dow Corning 3225C (dimethicone copolyol, 10% in cyclomethicone)

0.75 g of phenyltrimethicone (Dow Corning Fluid 556)

0.75 g of dimethicone (Dow Corning 200, 1000 cps)

0.5 g of SF 1214 (silicone gum, 15% in cyclomethicone, General Electric)

0.5 g of Dow Corning 2-8194 (24% amodimethicone, 7% cetyltrimethylammonium chloride, 8% Trideceth-12, 2% cyclodimethicone in water)

0.5 g of Cremophor RH410 (PEG-40 hydrogenated castor oil)

1.0 g of sodium chloride
0.1 g of citric acid
37.1 g of glycerol
to 100 g water

EXAMPLE 3

CLEAR HAIR CONDITIONER 16.0 g of cyclomethicone (Dow Corning 344)
6.0 g of Dow Corning 3225C (dimethicone copolyol, 10% in cyclomethicone)
1.0 g of 2-hydroxyethyl-2-hydroxy-3-(trimethylammonio)propyl ether cellulose chloride (polyquaternium 10, Polymer JR 400)
1.0 g of polyoxyethylene(20) sorbitan monolaurate (Polysorbate 20, Tween® 20)
0.8 g of sodium chloride
37.2 g of glycerol
to 100 g water

EXAMPLE 4

CLEAR HAIR CONDITIONER 16.0 g of cyclomethicone (Dow Corning 344)
6.0 g of Dow Corning 3225C (dimethicone copolyol, 10% in cyclomethicone)
2.0 g of Gafquat® 755N (polyquaternium 11, vinylpyrrolidone/dimethylaminoethyl methacrylate methosulfate copolymer, 20% in water)
1.0 g of polyoxyethylene(20) sorbitan monolaurate (Polysorbate 20, Tween® 20)
0.8 g of sodium chloride
37.2 g of glycerol
to 100 g water

EXAMPLE 5

CLEAR HAIR CONDITIONER 16.0 g of cyclomethicone (Dow Corning 344)
6.0 g of Dow Corning 3225C (dimethicone copolyol, 10% in cyclomethicone)
0.3 g of hydroxypropylguar hydroxypropyltrimonium chloride (Jaguar® C162)
1.0 g of polyoxyethylene(20) sorbitan monolaurate (Polysorbate 20, Tween® 20)
0.8 g of sodium chloride
37.9 g of glycerol
to 100 g water

EXAMPLE 6

CLEAR HAIR CONDITIONER 16.0 g of cyclomethicone (Dow Corning 344)
6.0 g of Dow Corning 3225C (dimethicone copolyol, 10% in cyclomethicone)
3.0 g of Luviquat® Care (polyquaternium 44, 3-methyl-1-vinyl-1H-imidazolium methylsulfate/vinylpyrrolidone copolymer, 7% in water)
1.0 g of polyoxyethylene(20) sorbitan monolaurate (Polysorbate 20, Tween® 20)
0.8 g of sodium chloride
36.2 g of glycerol
to 100 g water

What is claimed is:

1. Optically clear, transparent or translucent hair conditioner in the form of a water-in-silicone oil emulsion containing
   (A) at least one silicone surfactant consisting of at least one siloxane/polyoxyalkylene copolymers,
   (B) at least one hydrophobic nonsurfactant silicone compound in liquid form,
   (C) at least one basic or cationic nitrogen atom-containing hair-conditioning compound,
   (D) at least one nonionic silicone-free surfactant,
   (E) 15 to 50 wt. % of water,
   (F) 15 to 50 wt. % of at least one polyhydric alcohol and
   (G) at least one electrolyte.

2. Hair conditioner according to claim 1, wherein in that it is a microemulsion.

3. Hair conditioner according to claim 1, wherein in that the refractive indices of the oil phase and the aqueous phase are essentially equal.

4. Hair conditioner according to claim 1, wherein in that the hydro-phobic, nonsurfactant silicone compound (B) is selected from the group consisting of cyclic lydimethylsiloxanes, linear polydimethylsiloxanes, polydiethylsiloxanes, phenyl-substituted siloxanes, polymethylphenylsiloxanes, hydroxy-substituted siloxanes or mixtures thereof.

5. Hair conditioner according to claim 1, wherein in that it contains at least two hydrophobic, nonsurfactant silicone compounds (B), one of them being of low molecular weight and highly volatile and the other of high molecular weight and low-volatile or nonvolatile.

6. Hair conditioner according to claim 1, wherein in that the hair-conditioning compound (C) is selected from the group consisting of cationic surfactants, polymers with cationic or cationizable groups, cationically derivatized proteins or protein hydrolyzates, betaine and nitrogen-containing silicone compounds.

7. Hair conditioner according to claim 1, wherein in that it contains at least two hair-conditioning compounds (C) of which one is a cationic, silicone-free surfactant and the other a nitrogen-containing silicone compound.

8. Hair conditioner according to claim 6, wherein in that the cationic surfactant is consisting of at least one compounds of general formula (III)

$$N^{(+)}R^1R^2R^3R^4\ X^{(-)} \quad (III)$$

wherein
   $R^1$ to $R^4$ independently of each other denote aliphatic groups, aromatic groups, alkoxy groups, polyoxyalkylene groups, alkylamido groups, hydroxyalkyl groups, aryl groups or alkaryl groups, each with 1 to 22 carbon atoms, at least one of the $R^1$ to $R^4$ radicals having at least 8 carbon atoms, and
   $X^{(-)}$ denotes a cosmetically compatible anion.

9. Hair conditioner according to claim 6, wherein in that the nitrogen-containing silicone compound is selected from the group consisting of cationic silicone compounds, betaine silicone compounds and amino-substituted silicone compounds.

10. Hair conditioner according to claim 1, wherein in that the nonionic, silicone-free surfactant (D) is selected from the group consisting of ethoxylated fatty acids with 10 to 26 carbon atoms, ethoxylated monohydric or polyhydric alcohols with 1 to 6 carbon atoms, ethoxylated fatty alcohols with 10 to 26 carbon atoms, ethoxylated hydrogenated or non- hydrogenated castor oil, alkylpolyglucosides, glyceride alkoxylates, fatty acid glyceride polyalkylene glycol ethers or fatty acid partial glyceride polyalkylene glycol ethers, polyglycolamides, fatty acid sugar esters, ethoxylated fatty acid sugar esters and partial glycerides.

11. Hair conditioner according to claim 1, wherein in that the silicone surfactant (A) is present in an amount from 0.01 to 10 wt. %.

12. Hair conditioner according to claim 1, wherein in that the hydrophobic, nonsurfactant silicone compound (B) is present in an amount from 5 to 30 wt. %.

13. Hair conditioner according to claim 1, wherein in that the hair-conditioning compound (C) is present in an amount from 0.01 to 10 wt. %.

14. Hair conditioner according to claim 1, wherein in that the nonionic, silicone-free surfactant (D) is present in an amount from 0.01 to 5 wt. %.

15. Hair conditioner according to claim 1, wherein in that the aqueous phase contains at least one acid.

16. Hair conditioner according to claim 1, wherein in that it is in a transparent or translucent package.

* * * * *